US008858444B2

(12) United States Patent
Ogasawara et al.

(10) Patent No.: US 8,858,444 B2
(45) Date of Patent: Oct. 14, 2014

(54) CONTRAST ENHANCED ULTRASONOGRAPHY WITH SUPERIMPOSING DIFFERENT PHASES

(75) Inventors: Yoichi Ogasawara, Nasushiobara (JP);
Masatoshi Nishino, Otawara (JP);
Yutaka Kobayashi, Otawara (JP);
Takayuki Gunji, Otawara (JP)

(73) Assignees: Kabushiki Kaisha Toshiba, Tokyo (JP);
Toshiba Medical Systems Corporation, Otawara-shi (JP)

(*) Notice: Subject to any disclaimer, the term of this patent is extended or adjusted under 35 U.S.C. 154(b) by 782 days.

(21) Appl. No.: 12/794,055
(22) Filed: Jun. 4, 2010
(65) Prior Publication Data

US 2010/0312113 A1   Dec. 9, 2010

(30) Foreign Application Priority Data

Jun. 8, 2009 (JP) .................................. 2009-137703
May 10, 2010 (JP) .................................. 2010-108582

(51) Int. Cl.
| | | |
|---|---|---|
| A61B 8/08 | (2006.01) | |
| A61B 8/06 | (2006.01) | |
| A61B 8/13 | (2006.01) | |
| A61B 8/14 | (2006.01) | |
| G01S 7/52 | (2006.01) | |
| G06T 7/20 | (2006.01) | |
| A61B 8/00 | (2006.01) | |

(52) U.S. Cl.
CPC .............. *A61B 8/5253* (2013.01); *A61B 8/488* (2013.01); *A61B 8/483* (2013.01); *A61B 8/085* (2013.01); *A61B 8/0891* (2013.01); *A61B 8/481* (2013.01); *A61B 8/13* (2013.01); *A61B 8/14* (2013.01); *A61B 8/06* (2013.01); *G01S 7/52074* (2013.01); *G06T 7/2013* (2013.01); *A61B 8/4254* (2013.01); *A61B 8/4209* (2013.01); *A61B 8/08* (2013.01)
USPC ............................ 600/443; 600/437; 382/131

(58) Field of Classification Search
CPC ...... A61B 8/4209; A61B 8/4254; A61B 8/06; A61B 8/13; A61B 8/14; A61B 8/481; A61B 8/0891; A61B 8/483; A61B 8/488; G06T 7/2013
USPC ................................. 382/131; 600/437, 443
See application file for complete search history.

(56) References Cited

U.S. PATENT DOCUMENTS

| | | | |
|---|---|---|---|
| 6,659,953 B1 | 12/2003 | Sumanaweera et al. | |
| 2005/0215897 A1* | 9/2005 | Sakaguchi et al. | ............ 600/437 |

(Continued)

FOREIGN PATENT DOCUMENTS

| | | |
|---|---|---|
| JP | 63-242236 | 10/1988 |
| JP | 11-137552 | 5/1999 |

(Continued)

OTHER PUBLICATIONS

Lencioni et al. Tissue harmonic and contrast-specific imaging: back to gray scale in ultrasound. Eur. Radiol. (2002) 12:151-165.*

(Continued)

*Primary Examiner* — Long V. Le
*Assistant Examiner* — Helene Bor
(74) *Attorney, Agent, or Firm* — Oblon, Spivak, McClelland, Maier & Neustadt, L.L.P.

(57) ABSTRACT

When an image creating unit creates a three-dimensional ultrasound image of a blood-vessel early phase, an operator presses an image selecting button, and selects an area to be displayed as superimposed by using an image-selecting Graphical User Interface (GUI) displayed by an image-selecting GUI display-control unit. After the image creating unit start creation of a three-dimensional ultrasound image in a late phase, when the operator presses a composition display button, the movement-distance calculating unit calculates a movement distance between a three-dimensional tissue image at the moment of the press of the composition display button and each of three-dimensional tissue images in the area to be displayed as superimposed, and an image correcting unit corrects each of three-dimensional contrast enhanced images corresponding the three-dimensional tissue images of the blood-vessel early phase by using the movement distance. An animated-image compositing unit creates a group of images for animation that the corrected three-dimensional contrast enhanced images of the blood-vessel early phase are each combined with a three-dimensional contrast enhanced image of the late phase, and a monitor displays the group of the images for animation in animation.

16 Claims, 14 Drawing Sheets

(56) References Cited

U.S. PATENT DOCUMENTS

| | | | | |
|---|---|---|---|---|
| 2007/0230761 A1* | 10/2007 | Gundel et al. | | 382/131 |
| 2008/0292166 A1* | 11/2008 | Hirano et al. | | 382/131 |
| 2009/0080742 A1* | 3/2009 | Moriya | | 382/131 |
| 2010/0069756 A1 | 3/2010 | Ogasawara et al. | | |

FOREIGN PATENT DOCUMENTS

| | | |
|---|---|---|
| JP | 2002-238901 | 8/2002 |
| JP | 2004-000739 | 1/2004 |
| JP | 2004-112469 | 4/2004 |
| JP | 2004-147823 | 5/2004 |
| JP | 2004-321688 | 11/2004 |
| JP | 2005-528949 | 9/2005 |
| JP | 2006-122643 | 5/2006 |
| JP | 2006-141798 | 6/2006 |
| JP | 2007-160094 | 6/2007 |
| JP | 2009-072432 | 4/2009 |
| JP | 2009-095399 | 5/2009 |
| JP | 2009-119134 | 6/2009 |
| JP | 2009-183360 | 8/2009 |
| WO | 2007-040270 | 4/2007 |

OTHER PUBLICATIONS

Published by: Nago Bijutsu Insatsu Kabushiki Kaisha. "Medical Image/Radiological Equipment Hand Book," Japan Industries Association of Radiological Systems, 2001. 6 pages. (Partial English Translation of 5.9.1 Contrast Harmonic Imaging).

Office Action mailed Jan. 7, 2014, in Japanese Patent Application No. 2010-108582 (with English-language translation).

* cited by examiner

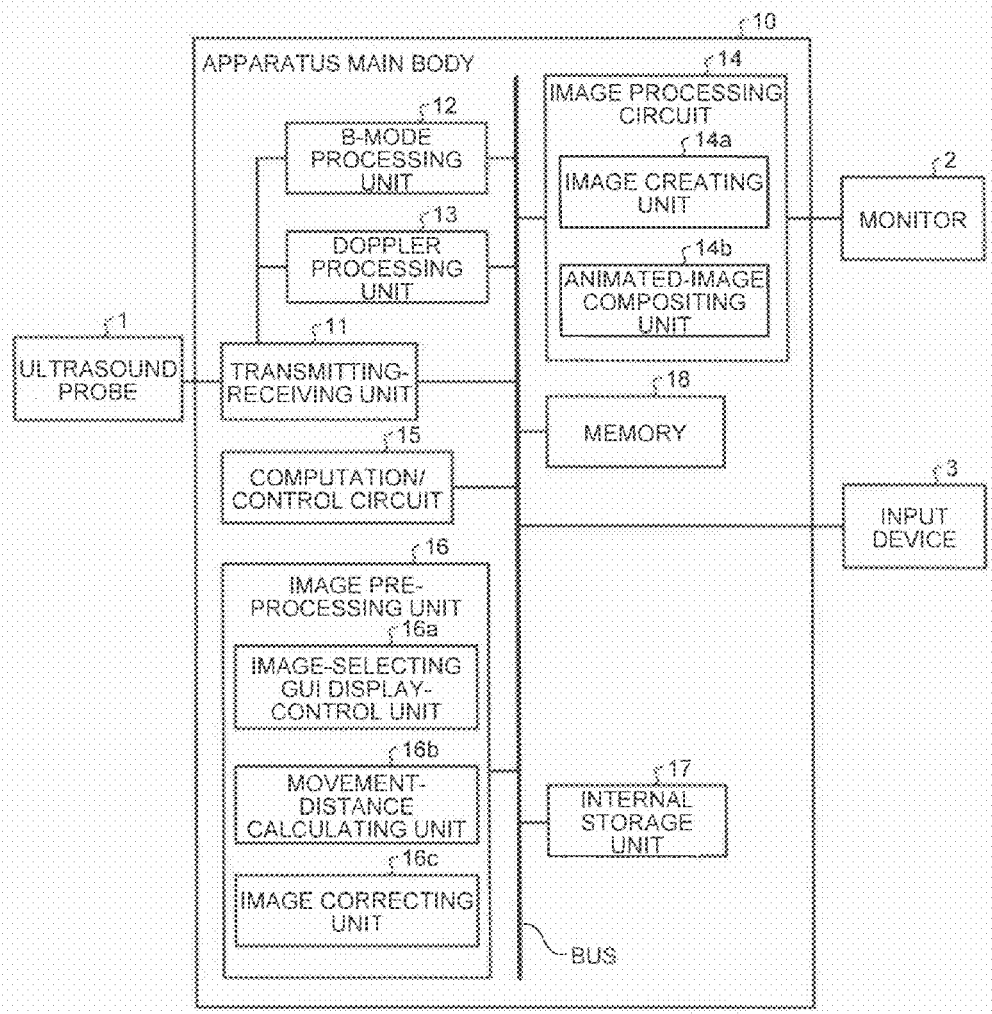

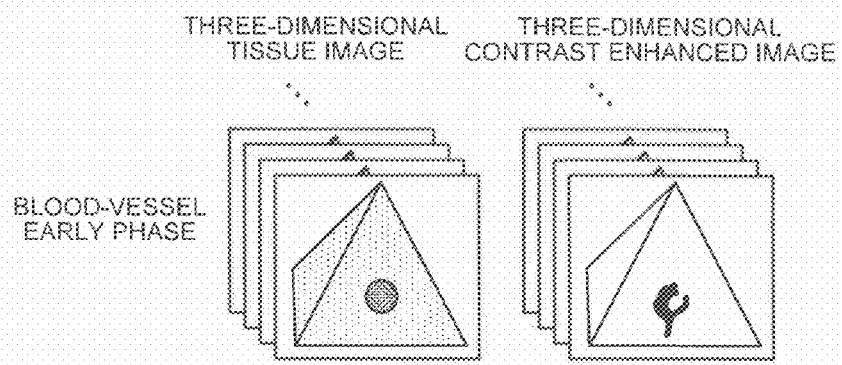

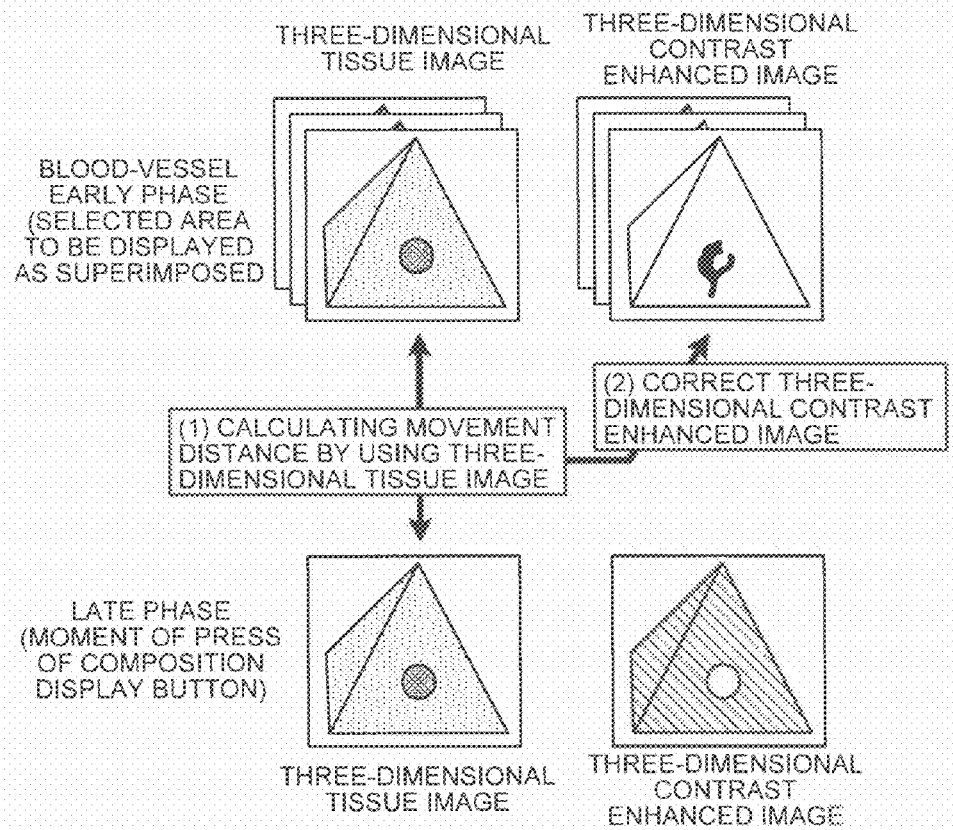

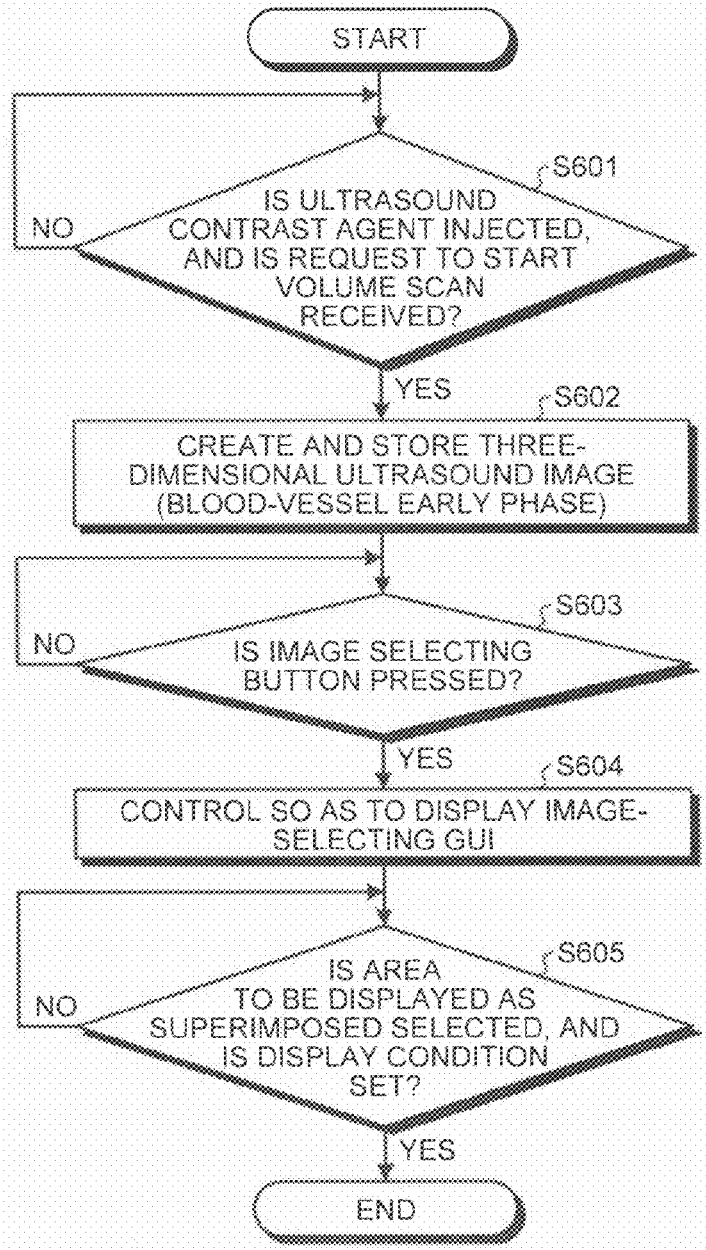

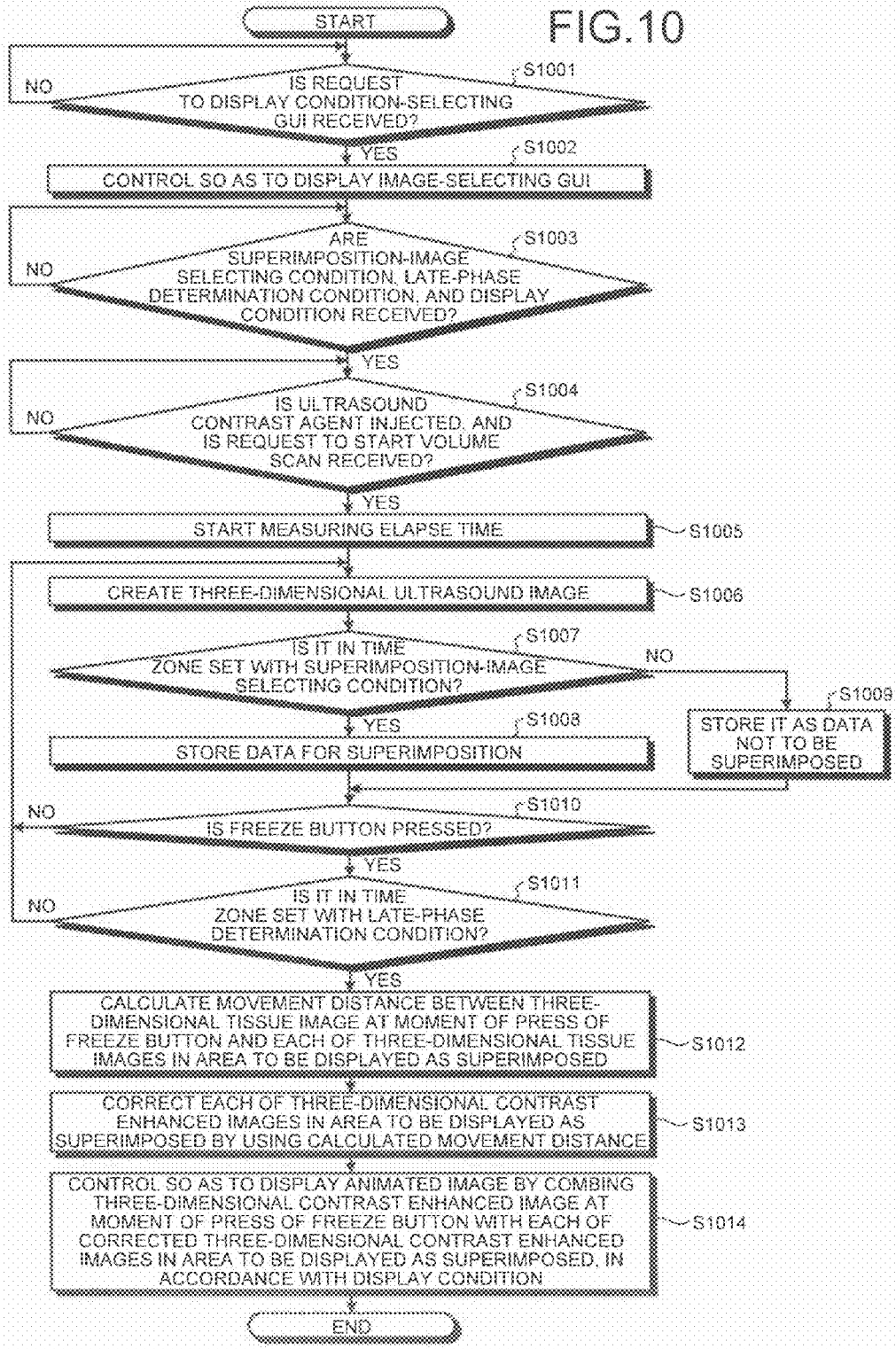

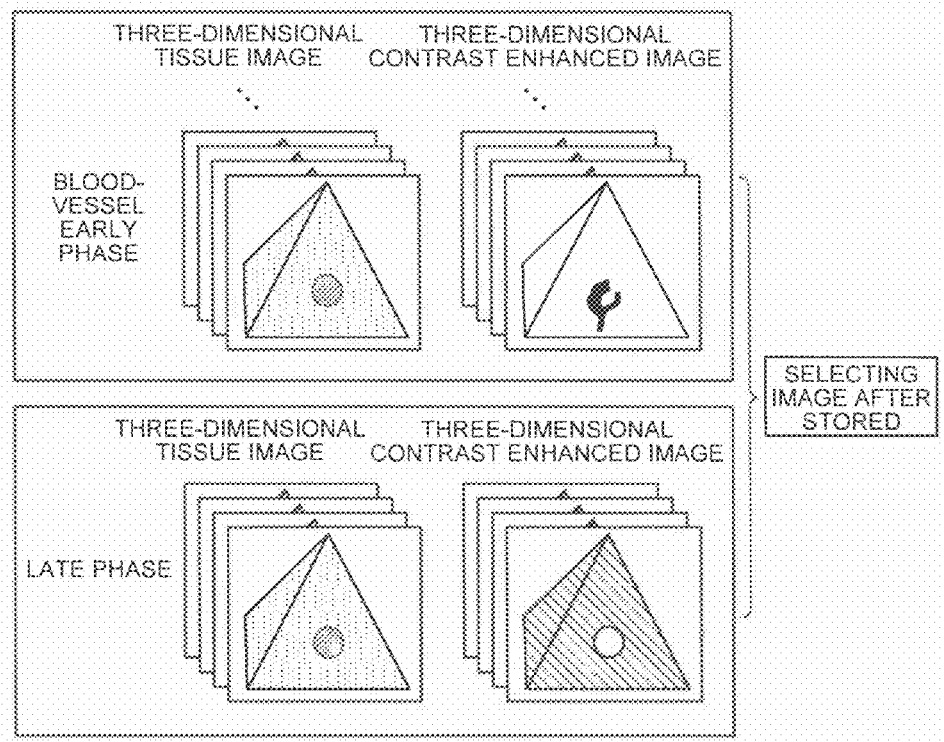

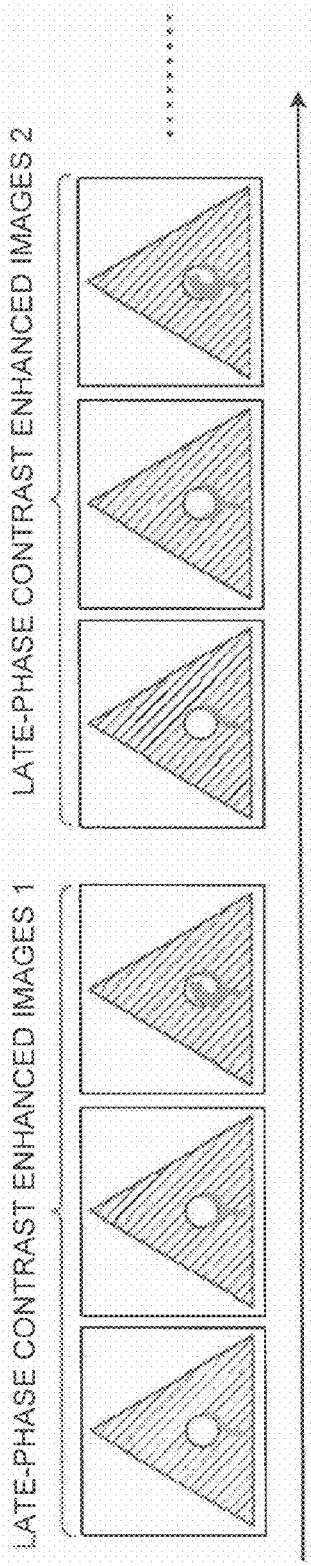

CONTRAST ENHANCED ULTRASONOGRAPHY WITH SUPERIMPOSING DIFFERENT PHASES

CROSS-REFERENCE TO RELATED APPLICATIONS

This application is based upon and claims the benefit of priority from Japanese Patent Application No. 2009-137703, filed on Jun. 8, 2009, and Japanese Patent Application No. 2010-108582, filed on May 10, 2010; the entire contents of all of which are incorporated herein by reference.

FIELD

Embodiments described herein relate generally to an ultrasound diagnosis apparatus, an image processing apparatus, an image processing method, and an image display method.

BACKGROUND

Conventionally, according to ultrasonography using an ultrasound diagnosis apparatus, contrast enhanced ultrasonography of taking an contrast enhanced image that is imaged of a blood flow with high sensitivity is performed by enhancing a blood flow signal with an ultrasound contrast agent of which main component is microbubbles (for example, see "Medical Image/Radiological Equipment Hand Book" edited by Japan Industries Association of Radiological Systems, published by Nago Bijutsu Insatsu Kabushiki Kaisha, 2001, pp. 221-225).

In a contrast enhanced ultrasonography of the abdomen of which object is a screening diagnosis on "benignancy and malignancy" of a hepatic tumor, it is recommended to evaluate contrast enhanced images taken in two phases, which are explained below, after giving a subject an ultrasound contrast agent that can be injected into a vein.

A first phase is a phase called an arterial phase or a blood-vessel early phase. The blood-vessel early phase corresponds to a period from an injection of an ultrasound contrast agent until several tens of seconds later, which is a phase in which an arterial blood flow can be dynamically observed owing to the injected ultrasound contrast agent.

Because a malignant hepatic tumor is mainly dominated by an artery, a doctor can confirm a structure of a blood vessel that nourishes a hepatic tumor by referring to a contrast enhanced image in a blood-vessel early phase. Particularly, in order to evaluate dynamics of the blood flow to the hepatic tumor, the doctor refers to an animated image of contrast enhanced images in the blood-vessel early phase by using an animation display function of the ultrasound diagnosis apparatus.

A second phase is a phase called a parenchymal phase or a late phase. The late phase corresponds to a period after approximately five minutes from an injection of a ultrasound contrast agent (after approximately four minutes in some facilities), which is a phase in which a distribution state of the ultrasound contrast agent remaining in the liver can be observed in a state that the ultrasound contrast agent in a blood flow is sufficiently reduced by pulmonary circulation.

It is known that a normal hepatic cell is dominated by a portal vein, in contrast to a malignant hepatic tumor, which is dominated by an artery as described above. Moreover, a normal hepatic cell includes a flow route of a blood flow in a fine structure, and additionally includes a macrophage that is called a Kupffer cell. By contrast, a malignant hepatic tumor loses a fine structure and a Kupffer cell that a normal hepatic cell has, in order to construct a unique tissue structure.

For this reason, the ultrasound contrast agent is taken by a macrophage into a normal hepatic tumor, in contrast, a degree of an intake of the ultrasound contrast agent into a malignant hepatic tumor is low. As a result, a high brightness part on a contrast enhanced image taken in the late phase is basically a signal obtained from a normal hepatic tumor. Therefore, the doctor can clearly observe the form of a hepatic tumor, by referring to the contrast enhanced image in the late phase. Particularly, in order to confirm a distribution of hepatic tumors, the doctor refers to a still image of the late phase that statically indicates a distribution of the ultrasound contrast agent, or a stereoscopic still image when using an ultrasound probe that can three-dimensionally scan with ultrasound.

Recently, in addition to screening a hepatic tumor, planning of an appropriate treatment course by diagnosing the malignancy (differentiation) of a hepatic tumor is desired. In such case, the doctor diagnoses the malignancy of a hepatic tumor by observing whether an inflow position of an artery in a contrast enhanced image taken in the blood-vessel early phase reaches the inside of the tumor or concentrates in a marginal region of the tumor, with respect to the hepatic tumor part that is a low-brightness part in a contrast enhanced image taken in the late phase.

For this reason, according to a conventional ultrasound diagnosis apparatus, as shown in FIG. 14, an animated image of contrast enhanced images taken in an arterial phase and a still image of a contrast enhanced image taken in an late phase are displayed in parallel, and the doctor observes the parallel-displayed contrast enhanced images, thereby performing screening of hepatic tumor and diagnosis of the malignancy. FIG. 14 is a schematic diagram for explaining the conventional technology.

However, contrast enhanced images in the blood-vessel early phase and the late phase displayed by the conventional ultrasound diagnosis apparatus are not always in the same cross section, and it is difficult to grasp precisely to which position in the tumor the artery invades because of parallel-display, the doctor cannot perform screening of hepatic tumor and diagnosis of the malignancy with precision.

To perform screening of hepatic tumor and diagnosis of the malignancy with precision, recently, reported is a "Re-Injection" method of by which after an ultrasound contrast agent is given at first time, and when reaching a late phase, the ultrasound contrast agent is then again given at the second time, a contrast enhanced image is taken on which an ultrasound contrast agent distribution in the arterial phase is newly displayed as superimposed over an ultrasound contrast agent distribution in the late phase.

However, according to the "Re-Injection" method described above, even though screening of hepatic tumor and diagnosis of the malignancy can be performed with precision, there is a problem that a physical burden onto a subject body and an operational burden onto a doctor increase because an ultrasound contrast agent is given twice, and an examination efficiency worsens because an examination time is extended.

BRIEF DESCRIPTION OF THE DRAWINGS

FIG. 1 is a schematic diagram for explaining a configuration of an ultrasound diagnosis apparatus according to a first embodiment;

FIG. 2 is a schematic diagram for explaining a three-dimensional tissue image and a three-dimensional contrast enhanced image in a blood-vessel early phase;

FIG. 4 is a schematic diagram for explaining a movement-distance calculating unit and an image correcting unit;

FIG. 6 is a flowchart for explaining image selecting processing by the ultrasound diagnosis apparatus according to the first embodiment;

FIG. 10 is a flowchart for explaining processing by the ultrasound diagnosis apparatus according to the second embodiment;

FIG. 11 is a schematic diagram for explaining a first modification of the embodiments;

FIG. 13 is a schematic diagram for explaining a third modification of the embodiments.

DETAILED DESCRIPTION

Figure 3A:
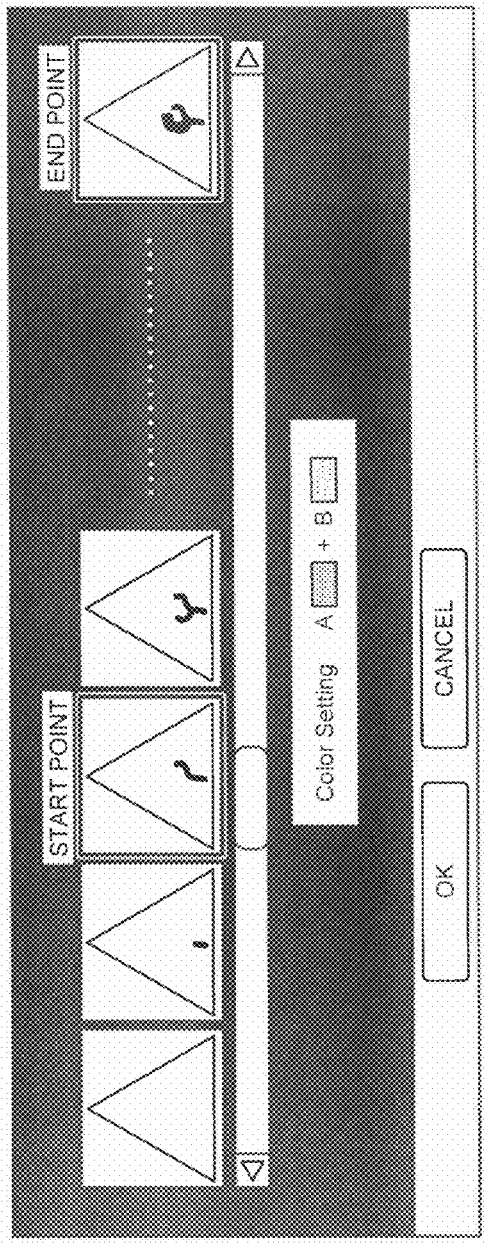
FIGS. 3A and 3B are schematic diagrams for explaining an image-selecting Graphical User Interface (GUI) display-control unit.

In one embodiment, an ultrasonic diagnostic apparatus includes a display control unit. The display control unit controls display such that an contrast enhanced image in a first phase and a contrast enhanced image in a second phase that is different from the first phase are superimposed and displayed on a certain display unit.

Exemplary embodiments of an ultrasound diagnosis apparatus, an image processing apparatus, an image processing method, and an image display method will be explained below in detail with reference to the accompanying drawings. The following description explains an ultrasound diagnosis apparatus into which an image processing apparatus that executes an image processing method and an image display method is integrated, as embodiments.

First of all, a configuration of an ultrasound diagnosis apparatus according to a first embodiment is explained below. FIG. 1 is a schematic diagram for explaining the ultrasound diagnosis apparatus according to the first embodiment. As shown in FIG. 1, the ultrasound diagnosis apparatus according to the embodiment includes an ultrasound probe 1, a monitor 2, an input device 3, and an apparatus main body 10.

The ultrasound probe 1 includes a plurality of built-in ultrasound vibration elements that is a plurality of vibration element cells, and transmits an ultrasound wave generated from the ultrasound vibration elements to the inside of a subject as an ultrasound beam. Moreover, the ultrasound probe 1 receives a reflected wave from internal tissue of the subject with each vibration element cell of the ultrasound vibration elements.

The embodiment is explained below in a case of two-dimensionally transmitting an ultrasound beam and three-dimensionally scanning the inside of a subject by using as the ultrasound probe 1 a two-dimensional ultrasound probe that includes a plurality of ultrasound vibration elements arranged in a matrix. Moreover, the two-dimensional ultrasound probe is capable of scanning the inside of the subject in a two-dimensional cross section by converging an ultrasound beam and transmitting it.

The embodiment can be applied to a case of using as the ultrasound probe 1 a mechanical scan probe that three-dimensionally scans the inside of a subject by mechanically oscillating a plurality of ultrasound vibration elements arranged in one row.

The monitor 2 is a display device that displays a Graphical User Interface (GUI) for an operator of the ultrasound diagnosis apparatus to input various setting requests by using the input device 3, and displays an ultrasound image created by the apparatus main body 10.

The input device 3 includes a mouse, a keyboard, a button, a panel switch, a touch command screen, a foot switch, a trackball, and the like, receives various setting requests from an operator of the ultrasound diagnosis apparatus, and transfers each of the received various setting requests to the apparatus main body 10.

For example, the input device 3 includes a "freeze button" as a button configured to be pressed by the operator. When the "freeze button" is pressed, transmission and reception of an ultrasound wave is temporarily terminated, so that the ultrasound diagnosis apparatus turns into a suspended state. Moreover, the input device 3 includes an "image selecting button" and a "composite-image display button", which are closely related to the embodiment, and will be described later in detail.

The apparatus main body 10 is a device that creates an ultrasound image based on a reflected wave received by the ultrasound probe 1; and includes a transmitting-receiving unit 11, a B-mode processing unit 12, a doppler processing unit 13, an image processing circuit 14, a computation/control circuit 15, an image pre-processing unit 16, an internal storage unit 17, and a memory 18, as shown in FIG. 1.

The transmitting-receiving unit 11 is connected to the ultrasound probe 1, and a pulsar (not-shown) built in the transmitting-receiving unit 11 generates a high voltage pulse at each predetermined time delay in accordance with the control by the computation/control circuit 15. High voltage pulses generated by the pulser built in the transmitting-receiving unit 11 are sequentially applied to each vibration element cell of the ultrasound vibration element built in the ultrasound probe 1, thereby generating an ultrasound wave at each vibration element cell.

Moreover, when a reception signal of the reflected wave received by the ultrasound probe 1 is input, the transmitting-receiving unit 11 performs a gain correction on the reception signal with a preamplifier (not-shown), and performs analog-to-digital (A/D) conversion processing on the reception signal of which gain is corrected. The transmitting-receiving unit 11 then temporarily stores the A/D-converted reception signal into the memory 18 via a bus.

Furthermore, the transmitting-receiving unit 11 reads the A/D-converted reception signal stored in the memory 18 with required timing in accordance with the control by the computation/control circuit 15, and turns the read A/D-converted reception signal into reception data by adding in a phased manner. The transmitting-receiving unit 11 then transmits the reception data to the B-mode processing unit 12 and the doppler processing unit 13 via the bus in accordance with the control by the computation/control circuit 15.

The B-mode processing unit 12 performs data creation processing for B-mode image composition for compositing a B-mode image on which a signal strength is expressed by the brightness, based on the received reception data. The doppler processing unit 13 performs data creation processing for doppler-mode image composition for compositing a doppler image on which moving object information is imaged, such as the average velocity, the distribution, the power, and the like, of such as blood flow, by using the doppler effect, based on the received reception data.

The B-mode processing unit 12 includes a frequency filter. The B-mode processing unit 12 separates a band signal of a fundamental wave corresponding to a transmission frequency among received data by using the frequency filter, and extracts a tissue signal inside the subject, thereby creating data for B-mode tissue image composition for compositing a tissue image in B-mode.

Moreover, the B-mode processing unit 12 separates a band signal of a subharmonic wave or a higher harmonic wave of a transmission frequency among received data by using frequency filtering, and extracts a signal that is enhanced by an ultrasound contrast agent, thereby creating data for B-mode contrast enhanced image composition for compositing a B-mode contrast enhanced image (hereinafter, "contrast enhanced image").

The B-mode processing unit 12 then transmits the created data for B-mode tissue-image composition and the created data for B-mode contrast enhanced image composition to the image processing circuit 14, and also stores them into the memory 18. Moreover, the doppler processing unit 13 transmits the created data for doppler-mode image composition to the image processing circuit 14, and also stores it into the memory 18.

The B-mode processing unit 12 and the doppler processing unit 13 can process both two-dimensional data and three-dimensional data, and perform data creation processing for three-dimensional image composition based on three-dimensional reception data created from reflected waves received by the ultrasound probe 1 that is a two-dimensional ultrasound probe, according to the embodiment.

The image processing circuit 14 includes an image creating unit 14*a* and an animated-image compositing unit 14*b*, as shown in FIG. 1. The image creating unit 14*a* creates B-mode images (a tissue image and a contrast enhanced image), and a doppler image, by performing conversion processing into a rectangular coordinate system (orthogonal conversion processing), or digital-to-analog (D/A) conversion processing, on data for image composition received from the B-mode processing unit 12 or the doppler processing unit 13.

When receiving data for three-dimensional image composition, the image creating unit 14*a* creates a three-dimensional B-mode image or a three-dimensional doppler image. Precisely, when the image creating unit 14*a* receives data for three-dimensional B-mode tissue image composition and data for three-dimensional B-mode contrast enhanced image composition from the B-mode processing unit 12, the image creating unit 14*a* creates a three-dimensional tissue image and a three-dimensional contrast enhanced image. Moreover, when the image creating unit 14*a* receives data for three-dimensional doppler image composition from the doppler processing unit 13, the image creating unit 14*a* creates a three-dimensional doppler image.

The animated-image compositing unit 14*b* performs animated-image composition by using images created by the image creating unit 14*a*. Specifically, the animated-image compositing unit 14*b* performs animated-image composition by using contrast enhanced images in a blood-vessel early phase and a late phase created by the image creating unit 14*a*. The animated-image compositing unit 14*b* will be described later in detail.

The image pre-processing unit 16 is a processing unit that performs pre-processing on an image created by the image creating unit 14*a* before animated-image composition processing is performed by the animated-image compositing unit 14*b*; and includes an image-selecting GUI display-control unit 16*a*, a movement-distance calculating unit 16*b*, and an image correcting unit 16*c*, as shown in FIG. 1. These will be described later in detail together with the animated-image compositing unit 14*b*.

The memory 18 is memory that stores data received from the transmitting-receiving unit 11, data received from the B-mode processing unit 12 and the doppler processing unit 13, and various images created by the image processing circuit 14.

The internal storage unit 17 stores various data, such as: various control conditions for performing ultrasound transmission and reception, image processing, and display processing; diagnosis information (for example, a patient ID, a doctor's opinion); and a diagnosis protocol. The internal storage unit 17 is configured to be used for storing images stored in the memory 18, as required.

The computation/control circuit 15 controls the whole processing by the ultrasound diagnosis apparatus, performed by the transmitting-receiving unit 11, the B-mode processing unit 12, the doppler processing unit 13, the image processing circuit 14, the image pre-processing unit 16, and the like, based on the various setting requests input from the input device 3 and various control conditions stored by the internal storage unit 17.

To perform contrast enhanced ultrasonography of abdomen, the ultrasound diagnosis apparatus according to the first embodiment creates a plurality of ultrasound images (three-dimensional tissue images and three-dimensional contrast enhanced images) along a time sequence based on reflected waves of ultrasound waves transmitted from the ultrasound probe 1 to the subject given with the ultrasound contrast agent. The ultrasound diagnosis apparatus according to the first embodiment then superimposes and displays a contrast enhanced image of the blood-vessel early phase and a contrast enhanced image of the late phase, thereby managing to perform screening of hepatic tumor and diagnosis of the malignancy with high precision efficiently.

Figure 3B:
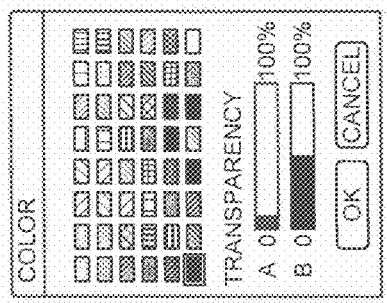
Figure 5A:
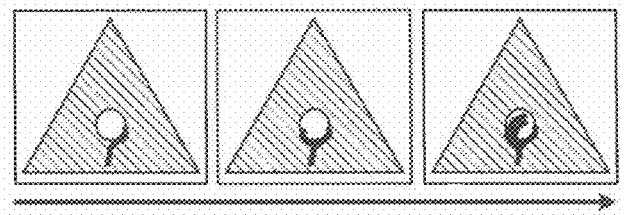
FIGS. 5A, 5B and 5C are schematic diagrams for explaining an animated-image compositing unit.
Figure 5B:
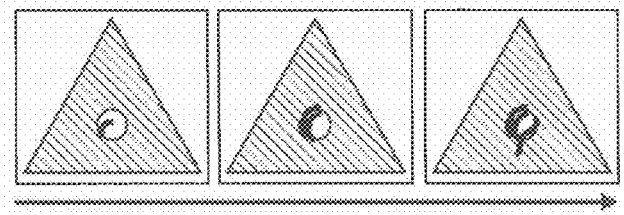
Figure 5C:
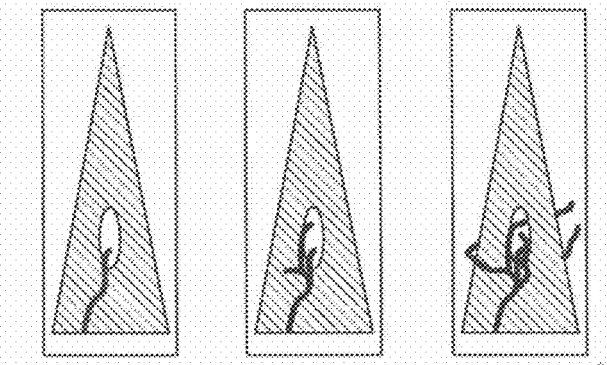

A concrete example of superimposed display processing performed by the ultrasound diagnosis apparatus according to the first embodiment is explained below with reference to FIGS. 2 to 5. FIG. 2 is a schematic diagram for explaining a three-dimensional tissue image and a three-dimensional contrast enhanced image in a blood-vessel early phase; FIGS. 3A and 3B are schematic diagrams for explaining an image-selecting GUI display-control unit; FIG. 4 is a schematic diagram for explaining a movement-distance calculating unit and an image correcting unit; and FIGS. 5A, 5B and 5C are schematic diagrams for explaining a animated-image compositing unit.

According to the first embodiment, to begin with, in a state that the ultrasound probe 1 is fixed on the abdomen of the subject by the operator, the ultrasound contrast agent is injected into a vein of the subject, and a three-dimensional scan (volume scan) is performed in a blood-vessel early phase (a period from the injection of the ultrasound contrast agent until several tens of seconds later).

Accordingly, the image creating unit 14*a* sequentially receives data for three-dimensional B-mode tissue image composition and data for three-dimensional B-mode contrast enhanced image composition from the B-mode processing unit 12, creates three-dimensional tissue images and three-dimensional contrast enhanced images along a time sequence in the blood-vessel early phase, as shown in FIG. 2, and stores the created images into the memory 18. As shown in FIG. 2, here on the three-dimensional contrast enhanced images of the blood-vessel early phase, blood-vessel dynamics of an artery are rendered. The image creating unit 14a also creates cross-sectional images (two-dimensional contrast enhanced images) in a certain cross-sectional direction from the created three-dimensional contrast enhanced images, and stores it into the memory 18.

When the "image selecting button" of the input device 3 is pressed here by the operator, the image-selecting GUI display-control unit 16a controls display such that an image selecting GUI as shown in FIG. 3A is displayed onto the monitor 2.

Specifically, the image-selecting GUI display-control unit 16a reads from the memory 18 the two-dimensional contrast enhanced images along a time sequence in the blood-vessel early phase created by the image creating unit 14a, and controls display such that the two-dimensional contrast enhanced images are displayed in parallel in a size-reduced state, as shown in FIG. 3A.

The operator selects here a group of two-dimensional contrast enhanced images to be subjected to composition processing by the animated-image compositing unit 14b. For example, as shown in FIG. 3A, the image-selecting GUI display-control unit 16a controls display such that when the operator selects an image to be a start point of the group of two-dimensional contrast enhanced images and an image to be an end point of the two-dimensional contrast enhanced images by using the trackball or the mouse of the input device 3, frames of the selected images are to be displayed in a highlighted manner. The contrast enhanced images to be displayed on the image-selecting GUI can be rendering images created by the image creating unit 14a through rendering processing, such as volume rendering processing, from three-dimensional contrast enhanced images.

Here, on the image-selecting GUI, as shown in FIG. 3A, "Color Setting" fields (A and B) for setting color tone in the composition processing by the animated-image compositing unit 14b are displayed. Precisely, "A of Color Setting" is a field for setting a color tone when compositing a contrast enhanced image in the blood-vessel early phase, and "B for Color Setting" is a field for setting a color tone (composite color) when compositing a contrast enhanced image in the late phase.

When a rectangular part of "A of Color Setting" or "B of Color Setting" is pressed by the operator, the image-selecting GUI display-control unit 16a causes display of a color palette for setting a composite color, as shown in FIG. 3B. When respective composite colors of the blood-vessel early phase and the late phase are selected by the operator who refers to the color palette, the image-selecting GUI display-control unit 16a causes the selected composite colors to be displayed in the fields of "Color Setting" shown in FIG. 3A.

Moreover, the image-selecting GUI display-control unit 16a causes display of a slide bar for setting transparency at a moment of composition in each of the blood-vessel early phase and the late phase, as well as the color palette, as shown in FIG. 3B. The operator sets transparency at a moment of composition in each of the blood-vessel early phase and the late phase, by moving the slide bar.

In this way, as a group of two-dimensional contrast enhanced images of the blood-vessel early phase to be subjected to composition processing is set by the operator who refers to the image-selecting GUI, a group of three-dimensional contrast enhanced images and a group of three-dimensional tissue images of the blood-vessel early phase in the area to be displayed as superimposed are determined.

When the ultrasound diagnosis apparatus then restarts a volume scan immediately before the late phase (a period after approximately five minutes from the injection of the ultrasound contrast agent) in accordance with an instruction by the operator, the image creating unit 14a sequentially receives data for three-dimensional B-mode tissue image composition and data for three-dimensional B-mode contrast enhanced image composition from the B-mode processing unit 12, and creates three-dimensional tissue images and three-dimensional contrast enhanced images along a time sequence in the late phase. On the three-dimensional contrast enhanced images in the late phase, a hepatic tumor part is rendered as a low brightness part.

The image creating unit 14a creates here a two-dimensional contrast enhanced image that is a cross-sectional image in a certain cross-sectional direction, from the three-dimensional contrast enhanced image in the late phase. The two-dimensional contrast enhanced image is displayed on the monitor 2 in accordance with the control by the computation/control circuit 15. When a composition display button of the input device 3 is then pressed by the operator who refers to two-dimensional contrast enhanced images of the late phase, transmission and reception of ultrasound wave is temporarily terminated, and processing by the movement-distance calculating unit 16b is started.

The movement-distance calculating unit 16b calculates a movement distance by using each of the three-dimensional tissue images of the blood-vessel early phase in the area to be displayed as superimposed selected by the operator who refers to the image-selecting GUI, and a three-dimensional tissue image corresponding to a two-dimensional contrast enhanced image at the moment of a press of the composition display button (see (1) in FIG. 4).

Specifically, the movement-distance calculating unit 16b calculates a movement distance of each three-dimensional tissue images of the blood-vessel early phase corresponding to a three-dimensional tissue image of the late phase. For example, the movement-distance calculating unit 16b performs binarization processing, edge processing, or filtering processing of extracting a feature amount on each of the selected three-dimensional tissue images, performs cross-correlation processing between the processed three-dimensional tissue images, thereby three-dimensionally calculating a movement distance of each of the three-dimensional tissue images of the blood-vessel early phase with respect to a corresponding three-dimensional tissue image of the late phase.

If a calculation throughput of the movement-distance calculating unit 16b is low, it can be set such that when calculating a movement distance, a computation volume is reduced by thinning out the number of sample points per scanning line. By contrast, if a calculation throughput of the movement-distance calculating unit 16b is high, when calculating a movement distance, a method of successive approximation can be used.

The image correcting unit 16c corrects each three-dimensional contrast enhanced image corresponding to each of the three-dimensional tissue images of the blood-vessel early phase in the area to be displayed as superimposed so as to match in position with a three-dimensional tissue image of the late phase at the moment of a press of the composition display button, by using a movement distance calculated by the movement-distance calculating unit 16b (see (2) in FIG. 4).

The animated-image compositing unit 14b combines a three-dimensional tissue image of the late phase at the moment of a press of the composition display button, and each of corrected three-dimensional contrast enhanced images in the area to be displayed as superimposed (the blood-vessel early phase) created by the image correcting unit 16c. In other words, the animated-image compositing unit 14b creates a group of images for animation on which blood-vessel dynamics of an artery nourishing a tumor change along a time sequence, with respect to a tumor part of which form is made clear. The animated-image compositing unit 14b performs composition processing in accordance with display conditions (composite color and transparency) set by the operator who refers to the image-selecting GUI.

For example, the animated-image compositing unit 14b causes the image creating unit 14a to create a corrected two-dimensional contrast enhanced image from each of corrected three-dimensional contrast enhanced images in the area to be displayed as superimposed (the blood-vessel early phase), in the same cross-sectional direction as that of a two-dimensional contrast enhanced image of the late phase referred by the operator at the moment of pressing the composition display button. The animated-image compositing unit 14b then combines the two-dimensional contrast enhanced image of the late phase and each of the corrected two-dimensional contrast enhanced images, thereby creating a group of images for animation, as shown in FIG. 5A.

Alternatively, the animated-image compositing unit 14b causes the image creating unit 14a to create a two-dimensional contrast enhanced image from a three-dimensional contrast enhanced image of the late phase and each of corrected three-dimensional contrast enhanced images in the area to be displayed as superimposed (the blood-vessel early phase), on a cross section orthogonal to the cross-sectional direction of a two-dimensional contrast enhanced image of the late phase referred by the operator at the moment of pressing the composition display button. Accordingly, as shown in FIG. 5B, the animated-image compositing unit 14b creates a group of images for animation on a cross section orthogonal to the cross section used in FIG. 5A.

Alternatively, the animated-image compositing unit 14b causes the image creating unit 14a to create volume rendering that volume rendering processing is performed in a view-point direction specified by the operator, from corrected three-dimensional contrast enhanced images in the area to be displayed as (the blood-vessel early phase). Furthermore, the animated-image compositing unit 14b causes the image creating unit 14a to create a two-dimensional contrast enhanced image on a cross section orthogonal to the view-point direction specified by the operator, from a three-dimensional contrast enhanced image at the moment of the press of the composition display button. Accordingly, as shown in FIG. 5C, the animated-image compositing unit 14b creates a group of images for animation depicting a state that an artery goes into the inside of a tumor.

The group of the images for animation created by the animated-image compositing unit 14b are then displayed in animation on the monitor 2 by the control of the computation/control circuit 15.

Figure 7:
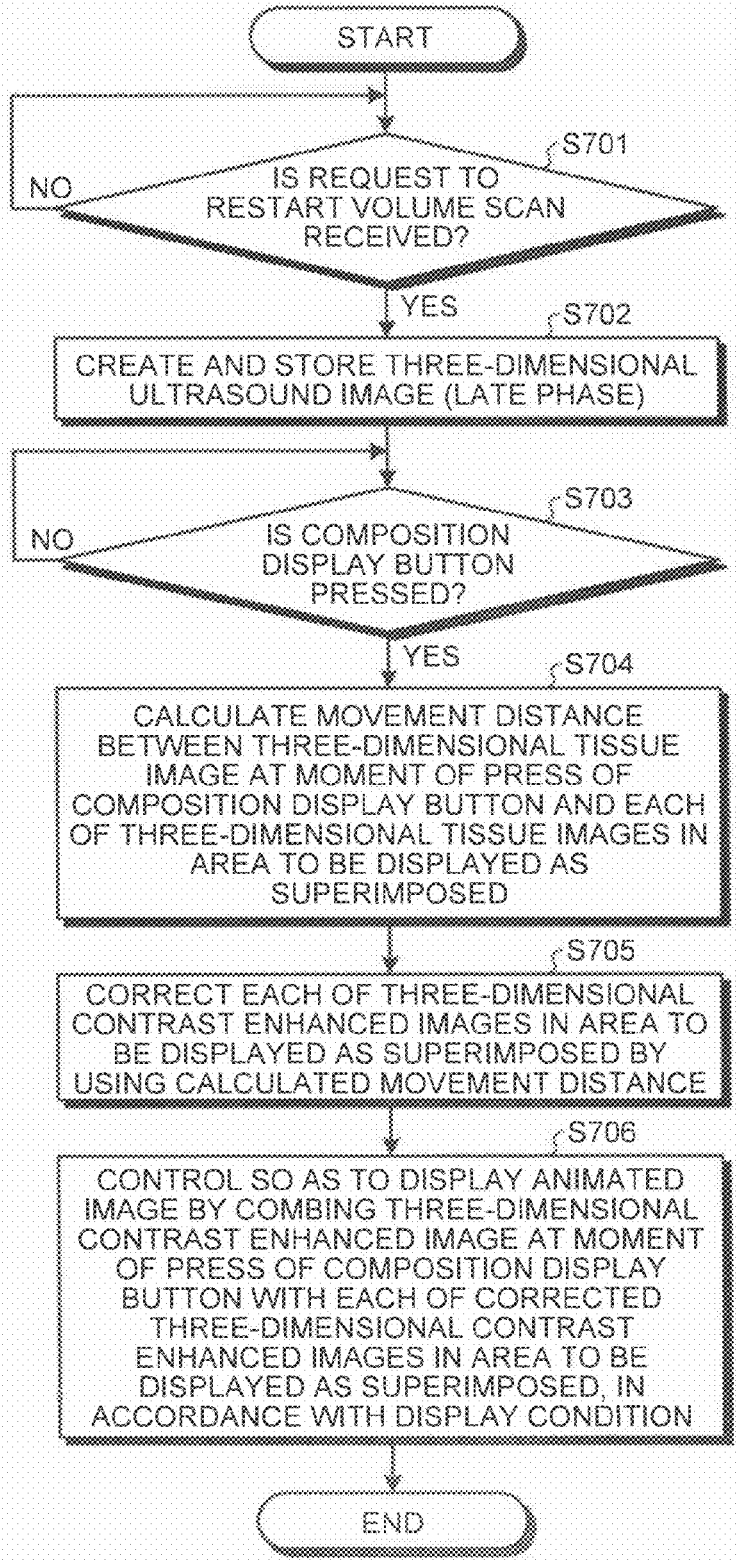
FIG. 7 is a flowchart for explaining animation display processing by the ultrasound diagnosis apparatus according to the first embodiment.

Processing by the ultrasound diagnosis apparatus according to the first embodiment is explained below with reference to FIGS. 6 and 7. FIG. 6 is a flowchart for explaining image selecting processing by the ultrasound diagnosis apparatus according to the first embodiment; and FIG. 7 is a flowchart for explaining animation display processing by the ultrasound diagnosis apparatus according to the first embodiment.

As shown in FIG. 6, when the ultrasound contrast agent is injected into the subject, and the ultrasound diagnosis apparatus according to the first embodiment receives a request to start a volume scan from the operator via the input device 3 (Yes at Step S601); the image creating unit 14a sequentially receives data for three-dimensional B-mode tissue image composition and data for three-dimensional B-mode contrast enhanced image composition from the B-mode processing unit 12, creates three-dimensional ultrasound images (three-dimensional tissue images and three-dimensional contrast enhanced images) along a time sequence in the blood-vessel early phase, and stores the created images into the memory 18 (Step S602). According to the embodiment, when the volume scan in the blood-vessel early phase is terminated, the ultrasound diagnosis apparatus temporarily stops transmission and reception of ultrasound wave in accordance with an instruction by the operator.

If the image selecting button of the input device 3 is pressed by the operator (Yes at Step S603); the image-selecting GUI display-control unit 16a performs control so as to display the image-selecting GUI on the monitor (Step S604, see FIGS. 3A and 3B).

After that, when an area to be displayed as superimposed is selected by the operator who refers to two-dimensional contrast enhanced images of the blood-vessel early phase displayed on the image-selecting GUI, and display conditions (composite color and transparency) are set (Yes at Step S605); the ultrasound diagnosis apparatus terminates the image selecting processing.

Subsequently, as shown in FIG. 7, when the ultrasound diagnosis apparatus according to the first embodiment receives a request to restart a volume scan from the operator via the input device 3 immediately before a late phase (Yes at Step S701); the image creating unit 14a sequentially receives data for three-dimensional B-mode tissue image composition and data for three-dimensional B-mode contrast enhanced image composition from the B-mode processing unit 12, creates three-dimensional ultrasound images (three-dimensional tissue images and three-dimensional contrast enhanced images) of the late phase, and stores the created images into the memory 18 (Step S702). Meanwhile, the monitor 2 is displaying a two-dimensional contrast enhanced image created by the image creating unit 14a from a three-dimensional contrast enhanced image in the late phase. When restarting the volume scan, the ultrasound probe 1 is arranged at the same position when the volume scan in the blood-vessel early phase is executed.

When the composition display button of the input device 3 is pressed by the operator (Yes at Step S703); the movement-distance calculating unit 16b calculates a movement distance between a three-dimensional tissue image corresponding to the two-dimensional contrast enhanced image at the moment of a press of the composition display button, and each of the selected three-dimensional tissue images of the blood-vessel early phase in the area to be displayed as superimposed selected by the operator who refers to the image-selecting GUI (Step S704).

After that, the image correcting unit 16c corrects each of the three-dimensional contrast enhanced images corresponding to the three-dimensional tissue images of the blood-vessel early phase in the area to be displayed as superimposed by using the movement distance calculated by the movement-distance calculating unit 16b, so as to match in position with the three-dimensional tissue image of the late phase at the moment of a press of the composition display button (Step S705).

Furthermore, the animated-image compositing unit 14b combines each of the corrected three-dimensional contrast enhanced images in the area to be displayed as superimposed (the blood-vessel early phase) created by the image correcting unit 16c with the three-dimensional contrast enhanced image of the late phase at the moment of a press of the composition display button in accordance with the display conditions; the computation/control circuit 15 controls display such that a group of images for animation created by the animated-image compositing unit 14b are to be displayed in animation on the monitor 2 (Step S706); and then the processing is terminated.

As described above, according to the first embodiment, the image creating unit 14a sequential receives data for three-dimensional B-mode tissue image composition and data for three-dimensional B-mode contrast enhanced image composition from the B-mode processing unit 12, and creates three-dimensional ultrasound images (three-dimensional tissue images and three-dimensional contrast enhanced images) along a time sequence in the blood-vessel early phase. When the image selecting button of the input device 3 is then pressed by the operator, the image-selecting GUI display-control unit 16a controls display such that the image-selecting GUI is displayed on the monitor. The operator who refers to the two-dimensional contrast enhanced images of the blood-vessel early phase displayed on the image-selecting GUI selects an area to be displayed as superimposed, and further sets display conditions (composite color and transparency).

The image creating unit 14a then sequentially receives data for three-dimensional B-mode tissue image composition and data for three-dimensional B-mode contrast enhanced image composition from the B-mode processing unit 12, and creates three-dimensional ultrasound images (three-dimensional tissue images and three-dimensional contrast enhanced images) of the late phase. When the composition display button of the input device 3 is pressed by the operator, the movement-distance calculating unit 16b calculates a movement distance between a three-dimensional tissue image corresponding to the two-dimensional contrast enhanced image at the moment of the press of the composition display button, and each of the selected three-dimensional tissue images of the blood-vessel early phase in the area to be displayed as superimposed selected by the operator who refers to the image-selecting GUI. The image correcting unit 16c then corrects each of the three-dimensional contrast enhanced images corresponding to the three-dimensional tissue images of the blood-vessel early phase in the area to be displayed as superimposed by using the movement distance calculated by the movement-distance calculating unit 16b.

The animated-image compositing unit 14b then combines each of the corrected three-dimensional contrast enhanced images in the area to be displayed as superimposed (the blood-vessel early phase) created by the image correcting unit 16c with the three-dimensional contrast enhanced image of the late phase at the moment of a press of the composition display button in accordance with the display conditions; and the computation/control circuit 15 controls display such that a group of images for animation created by the animated-image compositing unit 14b are to be displayed in animation on the monitor 2.

Consequently, according to the first embodiment, an animated image on which blood-vessel dynamics of an artery nourishing a tumor change along a time sequence is displayed with respect to a tumor part of which form is made clear, accordingly, the doctor can visually recognize a shape of the tumor and a distribution of nourishing blood vessels with respect to the tumor at the same time, thereby managing to perform screening of hepatic tumor and diagnosis of the malignancy with high precision efficiently.

Moreover, according to the first embodiment, because a group of images for animation are created in accordance with the set display conditions, visibility of the tumor and the nourishing blood vessels on the animated image can be improved, and screening of hepatic tumor and diagnosis of the malignancy can be performed with higher precision.

When an operator performing a two-dimensional scan by converging ultrasound beams with the two-dimensional ultrasound probe in order to refer to the late phase with a cross-sectional image, the ultrasound diagnosis apparatus according to the embodiment can automatically change transmitting-receiving conditions for ultrasound waves after the composition display button is pressed, and create a three-dimensional ultrasound image by executing a volume scan one time, thereby managing to perform processing by the movement-distance calculating unit 16b, the image correcting unit 16c, and the animated-image compositing unit 14b.

Figure 8:
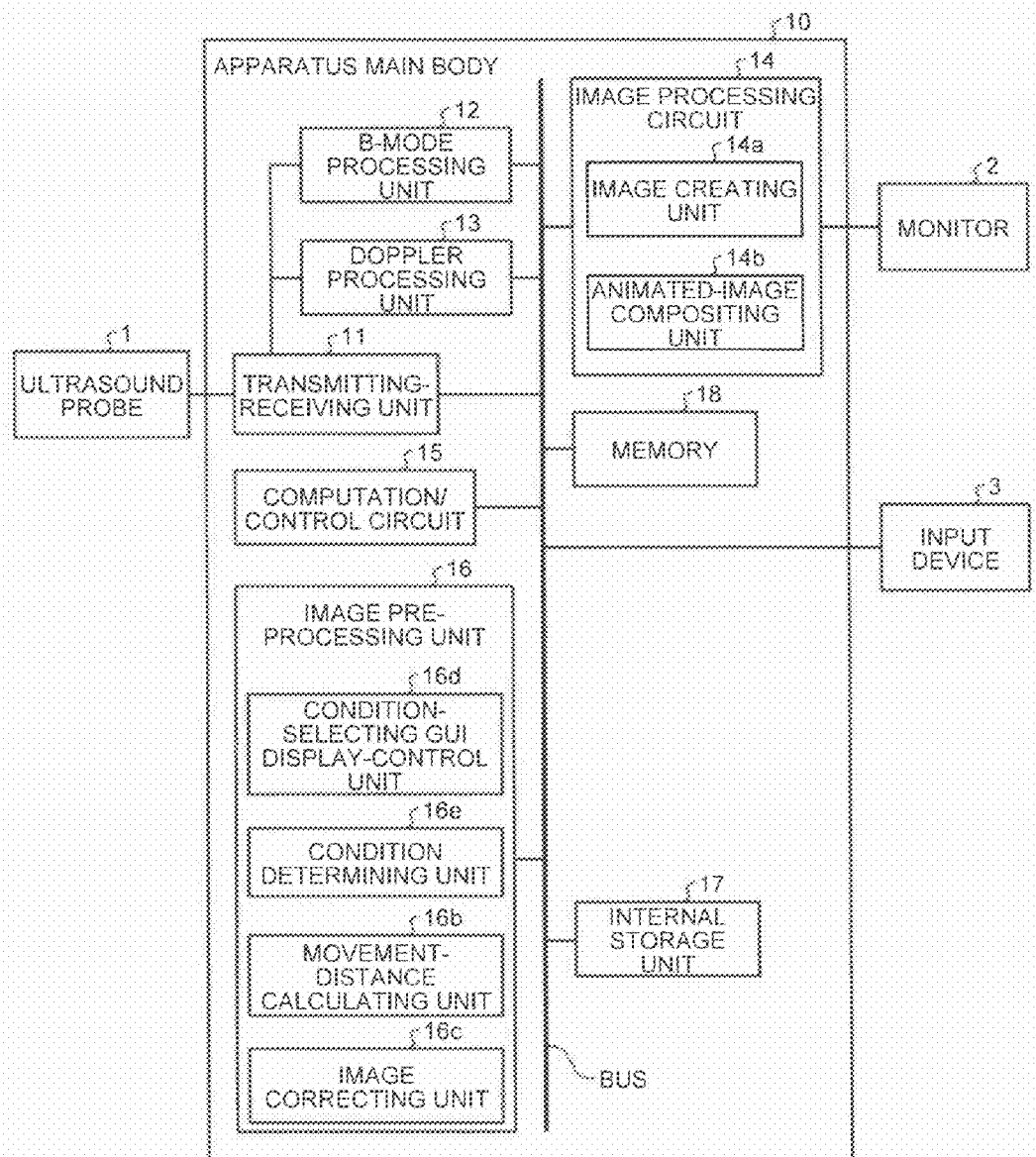
FIG. 8 is a schematic diagram for explaining a configuration of an ultrasound diagnosis apparatus according to a second embodiment.

The first embodiment described above is explained in a case where contrast enhanced images of the blood-vessel early phase to be displayed in animation are selected after an injection of the ultrasound contrast agent. A second embodiment is explained below in a case where contrast enhanced images of the blood-vessel early phase to be displayed in animation are selected in accordance with conditions set before an injection of the ultrasound contrast agent, with reference to FIGS. 8 and 9. FIG. 8 is a schematic diagram for explaining a configuration of an ultrasound diagnosis apparatus according to the second embodiment; and FIG. 9 is a schematic diagram for explaining a condition-setting GUI.

As shown in FIG. 8, the ultrasound diagnosis apparatus according to the second embodiment includes a condition-selecting GUI display-control unit 16d and a condition determining unit 16e instead of the image-selecting GUI display-control unit 16a, thereby being different from the ultrasound diagnosis apparatus according to the first embodiment. The following description explains mainly these.

When the operator presses a condition selecting button of the input device 3 before an injection of the ultrasound contrast agent, the condition-selecting GUI display-control unit 16d controls display such that a condition-selecting GUI is displayed on the monitor 2.

Figure 9:
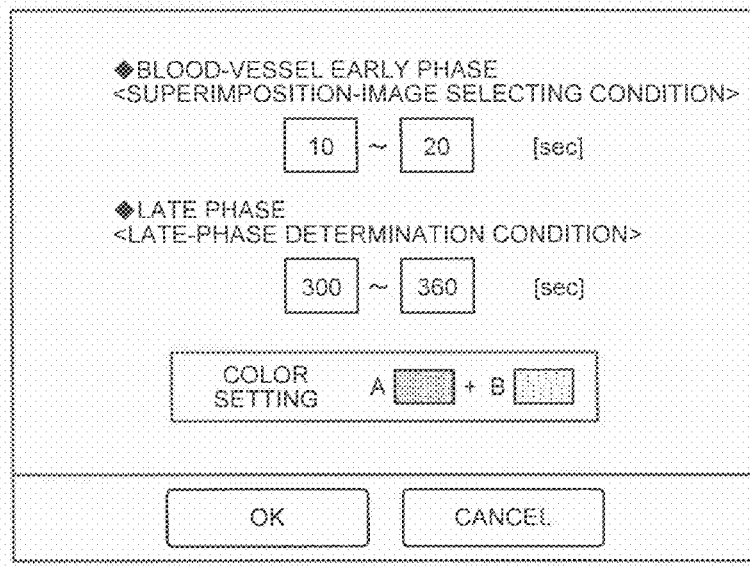
FIG. 9 is a schematic diagram for explaining a condition-setting GUI.

On the condition-selecting GUI, as shown in FIG. 9, entry fields for "superimposition-image selecting conditions" to input conditions for selecting an area to be displayed as superimposed in the blood-vessel early phase are displayed. For example, if it is intended to assign an ultrasound image that is created from 10 seconds to 20 seconds after an injection of the ultrasound contrast agent to an area to be displayed as superimposed, the operator inputs "10" and "20" into the entry fields for "superimposition-image selecting conditions".

Moreover, according to the second embodiment, an ultrasound image in the late phase is selected with a "freeze button" provided on a conventional ultrasound diagnosis apparatus, instead of the "composition display button" used in the first embodiment. In other words, according to the second embodiment, an ultrasound image that is displayed at the moment when the "freeze button" is pressed is subjected as subject data to movement-distance calculation and animated-image composition.

For this reason, as shown in FIG. 9, entry fields for "late-phase determination conditions" for inputting a condition to determine whether a moment at which the "freeze button" is pressed is the late phase are displayed on the condition-selecting GUI.

For example, if it is intended to set the late phase to "from 300 seconds to 360 seconds" after an injection of the ultrasound contrast agent, the operator inputs "300" and "360" into the entry fields for "late-phase determination conditions".

On the condition-selecting GUI, as shown in FIG. 9, the "Color Setting" fields (A and B) for setting color tone are displayed similarly to the image-selecting GUI explained in the first embodiment; and when the rectangular part of "A of Color Setting" or "B of Color Setting" is pressed by the operator, the color palette for setting a composite color is displayed together with the slide bar for setting the transparency.

The condition determining unit 16e measures an elapse time from the moment of an injection of the ultrasound contrast agent, in accordance with an instruction by the operator that is input simultaneously with the injection of the ultrasound contrast agent. The condition determining unit 16e then determines that a three-dimensional tissue image and a three-dimensional contrast enhanced image created from volume data collected in a time zone set with the "superimposition-image selecting conditions" are three-dimensional ultrasound images of the area to be displayed as superimposed" that is to be subjected to the processing by the movement-distance calculating unit 16b, the image correcting unit 16c, and the animated-image compositing unit 14b.

Moreover, the condition determining unit 16e determines whether the moment at which the "freeze button" is pressed is in a time zone set with the "late-phase determination conditions". If the moment at which the "freeze button" is pressed is in a time zone set with the "late-phase determination conditions", the condition determining unit 16e requests the movement-distance calculating unit 16b to execute movement-distance calculation processing. Accordingly, a composite animated image of the blood-vessel early phase and the late phase are displayed on the monitor 2.

On the other hand, if the moment at which the "freeze button" is pressed is not in a time zone set with the "late-phase determination conditions", the condition determining unit 16e requests the movement-distance calculating unit 16b not to execute movement-distance calculation processing. In such case, a message that notifies the operator that the present moment is not the time zone set with the "late-phase determination conditions" can be displayed on the monitor 2 in accordance with an instruction by the condition determining unit 16e.

Processing by the ultrasound diagnosis apparatus according to the second embodiment is explained below with reference to FIG. 10. FIG. 10 is a flowchart for explaining processing by the ultrasound diagnosis apparatus according to the second embodiment. The following description explains a case where an ultrasound image is created also in a portal-vein between the blood-vessel early phase and the late phase, without interrupting a volume scan.

As shown in FIG. 10, when the ultrasound diagnosis apparatus according to the second embodiment receives a request to display the condition-selecting GUI as the condition-selecting button is pressed before an injection of the ultrasound contrast agent (Yes at Step S1001); the condition-selecting GUI display-control unit 16d controls display such that the condition-selecting GUI is displayed on the monitor 2 (Step S1002).

When superimposition-image selecting conditions, late-phase determination conditions, and display conditions are then received from the operator via the condition-selecting GUI (Yes at Step S1003); the ultrasound diagnosis apparatus determines whether the ultrasound contrast agent is injected into the subject, and a request to start a volume scan is received from the operator via the input device 3 (Step S1004).

If request to start a volume scan is not received (No at Step S1004), the ultrasound diagnosis apparatus is on standby.

By contrast, if the request to start a volume scan is received (Yes at Step S1004); the condition determining unit 16e starts measuring an elapse time from the injection of the ultrasound contrast agent (Step S1005).

The image creating unit 14a then receives data for three-dimensional B-mode tissue image composition and data for three-dimensional B-mode contrast enhanced image composition from the B-mode processing unit 12, and creates three-dimensional ultrasound images (three-dimensional tissue images and three-dimensional contrast enhanced images) (Step S1006).

The condition determining unit 16e then determines whether the elapse time is a time zone set with the superimposition-image selecting conditions (Step S1007).

If it is not a time zone set with the superimposition-image selecting conditions (No at Step S1007); the condition determining unit 16e stores the created three-dimensional ultrasound images into the memory 18 as data not to be superimposed (Step S1009).

By contrast, if it is a time zone set with the superimposition-image selecting conditions (Yes at Step S1007); the condition determining unit 16e stores the created three-dimensional ultrasound images into the memory 18 as data to be superimposed (Step S1008).

After Step S1008 and Step S1009, the computation/control circuit 15 determines whether the "freeze button" is pressed (Step S1010).

If the "freeze button" is not pressed (No at Step S1010); returning to Step S1006, the image creating unit 14a receives data for three-dimensional B-mode tissue image composition and data for three-dimensional B-mode contrast enhanced image composition from the B-mode processing unit 12, and creates three-dimensional ultrasound images (three-dimensional tissue images and three-dimensional contrast enhanced images).

If the "freeze button" is pressed (Yes at Step S1010); the condition determining unit 16e determines whether the moment at which the "freeze button" is pressed is in a time zone set with the late-phase determination conditions (Step S1011).

If the moment at which the "freeze button" is pressed is not in a time zone set with the late-phase determination conditions (No Step S1011); returning to Step S1006, the image creating unit 14a receives data for three-dimensional B-mode tissue image composition and data for three-dimensional B-mode contrast enhanced image composition from the B-mode processing unit 12, and creates three-dimensional ultrasound images (three-dimensional tissue images and three-dimensional contrast enhanced images).

On the other hand, if the moment at which the "freeze button" is pressed is in a time zone set with the late-phase determination conditions (Yes at Step S1011); the movement-distance calculating unit 16b calculates a movement distance between a three-dimensional tissue image at the moment of the press of the "freeze button" and each of the three-dimensional tissue images in the area to be displayed as superimposed (Step S1012). In other words, until the "freeze button" is pressed in the time zone set with the late-phase determination conditions, the two-dimensional contrast enhanced image created from a three-dimensional contrast enhanced image by the image creating unit 14a is displayed on the monitor 2, based on the control by the computation/control circuit 15.

The image correcting unit 16c then corrects each of the three-dimensional contrast enhanced images corresponding the three-dimensional tissue images of the blood-vessel early phase in the area to be displayed as superimposed so as to match in position with the three-dimensional tissue image of the late phase at the moment of the press of the "freeze button", by using the movement distance calculated by the movement-distance calculating unit 16b (Step S1013).

After that, the animated-image compositing unit 14b combines the three-dimensional contrast enhanced image of the late phase taken at the moment of the press of the "freeze button" with each of the corrected three-dimensional contrast enhanced images in the area to be displayed as superimposed (the blood-vessel early phase) created by the image correcting unit 16c in accordance with the display conditions; the computation/control circuit 15 controls display such that a group of images for animation created by the animated-image compositing unit 14b are displayed in animation on the monitor 2 (Step S1014); and then the processing is terminated.

As described above, according to the second embodiment, as superimposition-image selecting conditions an late-phase determination conditions are set in advance, an animated image on which blood-vessel dynamics of an artery nourishing a tumor change along a time sequence is displayed only by pressing the "freeze button", accordingly, the doctor can easily perform screening of hepatic tumor and diagnosis of the malignancy with high precision.

The first and the second embodiments described above are explained in a case of displaying a composite animated image of the blood-vessel early phase and the late phase while performing contrast enhanced ultrasonography of abdomen. However, the first and the second embodiments described above can be in a case of displaying a composite animated image of the blood-vessel early phase and the late phase after performing contrast enhanced ultrasonography of abdomen. This is explained below with reference to FIG. 11. FIG. 11 is a schematic diagram for explaining a first modification of the embodiments.

The ultrasound diagnosis apparatus according to the first modification stores all of the three-dimensional tissue images and the three-dimensional contrast enhanced images that are created while performing the contrast enhanced ultrasonography of abdomen, into the memory 18 or the internal storage unit 17. The image creating unit 14a then creates, for example, a two-dimensional contrast enhanced image from a stored three-dimensional contrast enhanced image, and the monitor 2 displays the two-dimensional contrast enhanced image.

As shown in FIG. 11, the operator then selects the stored images, and the movement-distance calculating unit 16b, the image correcting unit 16c, and the animated-image compositing unit 14b execute respective processing by using the selected stored images, thereby displaying a composite animated image of the blood-vessel early phase and the late phase.

Figure 12A:
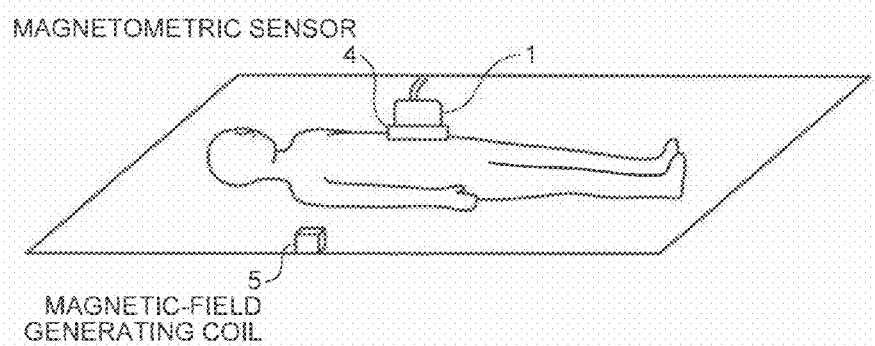
FIGS. 12A and 12B are schematic diagrams for explaining a second modification of the embodiments.
Figure 12B:
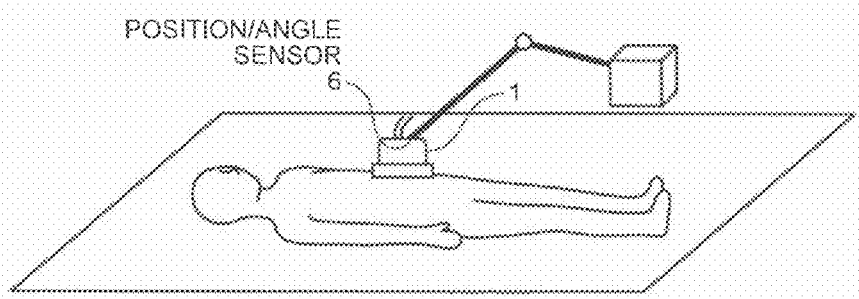
Figure 14:
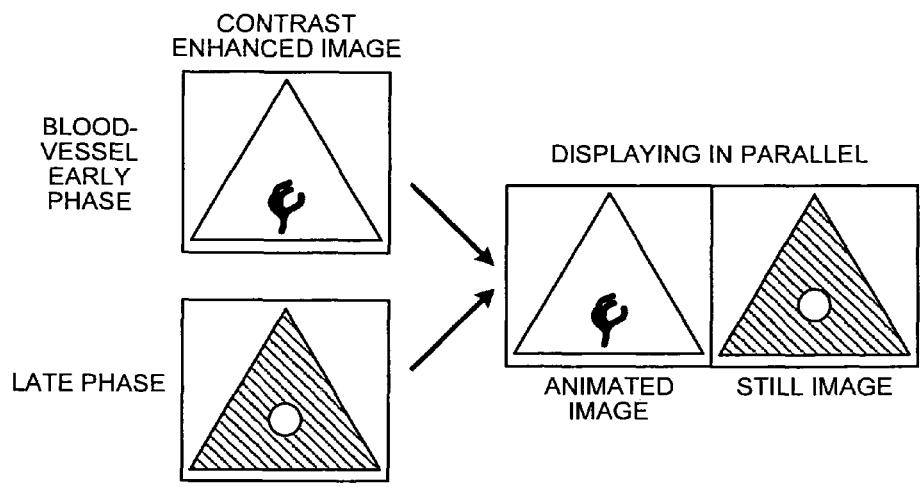
FIG. 14 is a schematic diagram for explaining a conventional technology.

Moreover, the first and the second embodiments described above are explained in a case where a movement distance between three-dimensional ultrasound images is calculated by image processing. However, the first and the second embodiments can be in a case where a movement distance between three-dimensional ultrasound images is calculated by various sensors attached to the ultrasound probe 1. This is explained below with reference to FIGS. 12A and 12B. FIGS. 12A and 12B are schematic diagrams for explaining a second modification of the embodiments.

In an ultrasound diagnosis apparatus according to the second modification, the ultrasound probe 1 is attached with a magnetometric sensor 4, as shown in FIG. 12A, and furthermore, a magnetic-field generating coil 5 that generates a magnetic signal is mounted to a bed on which a subject lies down. The magnetometric sensor 4 then detects the magnetic signal generated by the magnetic-field generating coil 5, and calculates a coordinate position with respect to the magnetic-field generating coil 5, thereby calculating a movement distance of the ultrasound probe 1. The image correcting unit 16c then executes correction processing of a three-dimensional contrast enhanced image by using the movement distance calculated by the magnetometric sensor 4.

Alternatively, in the ultrasound diagnosis apparatus according to the second modification, for example, as shown in FIG. 12B, the ultrasound probe 1 is connected to an arm. The arm is attached with a position/angle sensor 6. The position/angle sensor 6 detects a position of the ultrasound probe 1 with respect to the bed, and an angle of the ultrasound probe 1 with respect to the bed. The image correcting unit 16c then executes correction processing of a three-dimensional contrast enhanced image by using the movement distance of the position and the angle calculated by the position/angle sensor 6.

Furthermore, the first and the second embodiments described above are explained in a case where movement-distance calculation processing of each three-dimensional tissue image in an area to be displayed as superimposed manner is performed by using a three-dimensional tissue image of the late phase that is created at a time point specified by the operator. However, the first and the second embodiments described above can be in a case where each time when a three-dimensional tissue image is newly created in the late phase, movement-distance calculation processing of each three-dimensional tissue image is performed by using the three-dimensional tissue image. This is explained below with reference to FIG. 13. FIG. 13 is a schematic diagram for explaining a third modification of the embodiments.

An ultrasound diagnosis apparatus according to the third modification performs movement-distance calculation processing, correction processing, image composition processing, and display control processing in real time each time when a three-dimensional tissue image of the late phase and a three-dimensional contrast enhanced image are newly created. For example, each time when a three-dimensional tissue image and a three-dimensional contrast enhanced image are newly created at and after a time point turning into the late phase, the movement-distance calculating unit 16b calculates a movement distance between the newly-created three-dimensional tissue image of the late phase and each of the three-dimensional tissue images in the area to be displayed as superimposed. The image correcting unit 16c then corrects each of three-dimensional contrast enhanced images corresponding to each of the three-dimensional tissue images of the blood-vessel early phase in the area to be displayed as superimposed, so as to match in position with a three-dimensional contrast enhanced image created together with the three-dimensional tissue image of the late phase used for the movement-distance calculation processing. The animated-image compositing unit 14b then combines the new three-dimensional contrast enhanced image of the late phase with each of the corrected three-dimensional contrast enhanced images in the area to be displayed as superimposed. The computation/control circuit 15 then controls display such that a group of images for animation that are created with respect to each of the new three-dimensional contrast enhanced images of the late phase are displayed on the monitor 2 in animation. Accordingly, as shown in FIG. 13, the monitor 2 displays a group of images for animation of late-phase contrast enhanced images 1, and a group of images for animation of late-phase contrast enhanced images 2, in real time.

Moreover, the first and the second embodiments described above are explained in a case where a processing subject to the processing by the movement-distance calculating unit 16b, the image correcting unit 16c and the animated-image compositing unit 14b is the whole data created through a volume scan. However, the first and the second embodiments described above can be in a case where a processing subject to the processing by the movement-distance calculating unit 16b, the image correcting unit 16c and the animated-image compositing unit 14b is only a region of interest set by the operator among the data created through a volume scan.

Furthermore, the first and the second embodiments described above are explained in a case where a plurality of ultrasound images in the blood-vessel early phase are selected along a time sequence. However, the first and the second embodiments described above can be in a case where only one of ultrasound images in the blood-vessel early phase is selected. In such case, although a composite image to be displayed is a still image, by selecting a contrast enhanced image of the blood-vessel early phase at an appropriate time point, screening of hepatic tumor and diagnosis of the malignancy with high precision can be efficiently performed.

Moreover, the first and the second embodiments described above are explained in a case where a cross-sectional view created from a three-dimensional contrast enhanced image of the late phase is subjected to image composition. However, the first and the second embodiments described above can be in a case where a rendering image created from a three-dimensional contrast enhanced image of the late phase is subjected to image composition.

Furthermore, the first and the second embodiments described above are explained in a case of using a three-dimensional ultrasound image that is created through a volume scan. However, the first and the second embodiments described above can be in a case of using a two-dimensional ultrasound image that is created through a two-dimensional scan by finding an appropriate observational cross-section direction.

The components of each device shown in the drawings are conceptual for describing functions, and not necessarily to be physically configured as shown in the drawings. In other words, concrete forms of distribution and integration of the units are not limited to those shown in the drawings, and all or part of the units can be configured to be functionally or physically distributed and integrated in an arbitrary unit depending on various loads and conditions in use.

While certain embodiments have been described, these embodiments have been presented by way of example only, and are not intended to limit the scope of the inventions. Indeed, the novel apparatuses and methods described herein may be embodied in a variety of other forms; furthermore, various omissions, substitutions and changes in the form of the apparatuses and methods described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus comprising:
   a processor connected to a memory,
   wherein the processor is configured to:
   calculate a movement distance between a tissue image in a first phase appearing after an ultrasound contrast agent is given to a subject, and a tissue image in a second phase that is a phase later than the first phase;
   create a corrected image from a contrast enhanced image in the first phase by matching the contrast enhanced image in the first phase in position with a contrast enhanced image in the second phase based on the movement distance;
   create a composite image by combining the corrected image and the contrast enhanced image in the second phase; and
   control a display unit to display the composite image, wherein
   the tissue image in the first phase is an ultrasound image created by separating a fundamental wave corresponding to a transmission frequency of ultrasound waves transmitted from an ultrasound probe onto the subject in the first phase from reflected waves of the ultrasound waves in the first phase,
   the tissue image in the second phase is an ultrasound image created by separating the fundamental wave corresponding to the transmission frequency of ultrasound waves transmitted from the ultrasound probe onto the subject in the second phase from reflected waves of the ultrasound waves in the second phase,
   the contrast enhanced image in the first phase is an ultrasound image created by separating a subharmonic wave or a higher harmonic wave of the transmission frequency from the reflected waves used for creating the tissue image in the first phase, and
   the contrast enhanced image in the second phase is an ultrasound image created by separating the subharmonic wave or the higher harmonic wave of the transmission frequency separated from the reflected waves used for creating the tissue image in the second phase.

2. The ultrasound diagnosis apparatus according to claim 1, further comprising
   an input unit that receives an instruction of an operator to select a group of selected contrast enhanced images in the first phase from a plurality of contrast enhanced images that is already created along a time sequence in the first phase, wherein the processor is further configured to:
   calculate each movement distance between each of a group of selected tissue images in the first phase and the tissue image in the second phase, each of the selected tissue images in the first phase is already created together with each of the selected contrast enhanced images in the first phase,
   create a group of corrected contrast enhanced images by matching each of the selected contrast enhanced images in the first phase in position with the contrast enhanced image in the second phase created together with the tissue image in the second phase used for movement-distance calculation processing, based on respective movement distances of the selected tissue images in the first phase,
   create a group of composite images by combining each of the corrected contrast enhanced images and the contrast enhanced image in the second phase, and
   control the display unit to display the group of the composite images in animation.

3. The ultrasound diagnosis apparatus according to claim 2, wherein the processor is further configured to perform movement-distance calculation processing by using the tissue image that is created at a moment specified by the operator via the input unit in the second phase, or performs movement-distance calculation processing each time when the tissue image is newly created in the second phase by using the newly created tissue image.

4. The ultrasound image diagnosis apparatus according to claim 3, wherein the controlling the display unit switches an image displayed on the display unit from the contrast enhanced image in the second phase to the composite image based upon the input unit receiving a composition display request from the operator during a scan in the second phase.

5. The ultrasound diagnosis apparatus according to claim 2, wherein
when creating three-dimensional tissue images and three-dimensional contrast enhanced images along a time sequence by three-dimensionally scanning with the ultrasound waves by the ultrasound probe, the processor is further configured to:
calculate each movement distance between each of a group of selected three-dimensional tissue images in the first phase corresponding to the group of the selected tissue images in the first phase and a three-dimensional tissue image in the second phase corresponding to the tissue image in the second phase,
create a group of corrected three-dimensional contrast enhanced images by matching each of selected three-dimensional contrast enhanced images in the first phase, corresponding to each of the selected contrast enhanced images in the first phase, in position with a three-dimensional contrast enhanced image in the second phase corresponding to the contrast enhanced image in the second phase based on respective movement distances of the group of the selected three-dimensional tissue images in the first phase, and
create the group of composite images by combining a cross-sectional image of the three-dimensional contrast enhanced image in the second phase corresponding to a set cross section that is arbitrarily set and respective cross-sectional images of the corrected three-dimensional contrast enhanced images corresponding to the set cross section, or by combining the cross-sectional image of the three-dimensional contrast enhanced image in the second phase corresponding to the set cross section and respective images of the corrected three-dimensional contrast enhanced images.

6. The ultrasound diagnosis apparatus according to claim 5, wherein the processor is further configured to perform movement-distance calculation processing by using the three-dimensional tissue image that is created at a time point specified by the operator via the input unit in the second phase, or performs movement-distance calculation processing each time when the three-dimensional tissue image is newly created in the second phase by using the newly created three-dimensional tissue image.

7. The ultrasound image diagnosis apparatus according to claim 6, wherein, based upon the input unit receiving a composition display request from the operator performing a two-dimensional scan during a scan in the second phase, the controlling the display unit controls the ultrasound probe to execute a three-dimensional scan in order to display the composite image on the display unit.

8. The ultrasound diagnosis apparatus according to claim 1, wherein the processor is further configured to:
calculate each movement distance between each of a group of selected tissue images that are a group of tissue images in the first phase created in a selection period set in advance by the operator via an input unit, and the tissue image of the second phase,
create a group of corrected contrast enhanced images that a group of selected contrast enhanced images that are a group of the selected contrast enhanced images corresponding to the group of the selected tissue images are each corrected so as to match in position with the contrast enhanced image corresponding to the tissue image of the second phase used for movement-distance calculation, based on respective movement distances of the selected tissue images,
create a group of composite images each of which is composited of each of the corrected contrast enhanced images and the contrast enhanced image corresponding to the tissue image of the second phase, and
control the display such that the group of the composite images are displayed in animation on the display unit.

9. The ultrasound diagnosis apparatus according to claim 8, wherein the processor is further configured to perform movement-distance calculation processing by using a tissue image that is created at a moment specified by the operator via the input unit in the second phase, or performs movement-distance calculation processing each time when a tissue image is newly created in the second phase by using created tissue image.

10. The ultrasound diagnosis apparatus according to claim 8, wherein
when creating three-dimensional tissue images and three-dimensional contrast enhanced images along a time sequence by three-dimensionally scanning with the ultrasound waves by the ultrasound probe, the processor is further configured to:
calculate each movement distance between each of a group of selected three-dimensional tissue images in the first phase corresponding to the group of selected tissue images in the first phase and a three-dimensional tissue image in the second phase corresponding to the tissue image in the second phase,
create a group of corrected three-dimensional contrast enhanced images by matching each of selected three-dimensional contrast enhanced images in the first phase, corresponding to each of the selected contrast enhanced images in the first phase, in position with a three-dimensional contrast enhanced image in the second phase corresponding to the contrast enhanced image in the second phase based on respective movement distances of the group of the selected three-dimensional tissue images, and
create a group of composite images by combining a cross-sectional image of the three-dimensional contrast enhanced image in the second phase corresponding to a set cross section that is arbitrarily set and respective cross-sectional images of the corrected three-dimensional contrast enhanced images corresponding to the set cross section, or by combining the cross-sectional image of the three-dimensional contrast enhanced image in the second phase corresponding to the set cross section and respective images of the corrected three-dimensional contrast enhanced images.

11. The ultrasound diagnosis apparatus according to claim 10, wherein the processor is further configured to perform movement-distance calculation processing by using three-dimensional tissue images that are created at a time point specified by the operator via the input unit in the second phase, or performs movement-distance calculation processing each time when a three-dimensional tissue image is newly created in the second phase by using the three-dimensional tissue image.

12. The ultrasound diagnosis apparatus according to claim 1, further comprising
an input unit that receives an instruction of an operator to select a group of selected contrast enhanced images in the first phase from a plurality of contrast enhanced images that is already created along a time sequence in the first phase and to specify a specified contrast enhanced images in the second phase from a plurality of contrast enhanced images that is already created along a time sequence in the second phase, wherein the processor is further configured to:

calculate each movement distance between each of a group of selected tissue images in the first phase and a specified tissue image in the second phase, each of the selected tissue images in the first phase is already created together with each of the selected contrast enhanced images in the first phase and the specified tissue image in the second phase is already created together with the specified contrast enhanced image in the second phase, create a group of corrected images by matching each of the selected contrast enhanced images in the first phase in position with the specified contrast enhanced image in the second phase, based on respective movement distances of the selected tissue images in the first phase, create a group of composite images by combining each of the corrected contrast enhanced images and the specified contrast enhanced image in the second phase, and control the display unit to display the group of the composite images in animation.

13. The ultrasound diagnosis apparatus according to claim 12, wherein when creating three-dimensional tissue images and three-dimensional contrast enhanced images along a time sequence by three-dimensionally scanning with the ultrasound waves by the ultrasound probe, the processor is further configured to:

calculate each movement distance between each of a group of selected three-dimensional tissue images in the first phase corresponding to the group of the selected tissue images in the first phase and a specified three-dimensional tissue image in the second phase corresponding to the specified contrast enhanced images in the second phase, create a group of corrected three-dimensional contrast enhanced images by matching each of selected three-dimensional contrast enhanced images in the first phase, corresponding to each of the selected contrast enhanced images in the first phase, in position with a specified three-dimensional contrast enhanced image in the second phase corresponding to the specified contrast enhanced image in the second phase based on respective movement distances of the group of the selected three-dimensional tissue images, and create the group of composite images by combining a cross-sectional image of the specified three-dimensional contrast enhanced image in the second phase corresponding to a set cross section that is arbitrarily set and respective cross-sectional images of the corrected three-dimensional contrast enhanced images corresponding to the set cross section, or by combining the specified cross-sectional image of the three-dimensional contrast enhanced image in the second phase corresponding to the set cross section and respective images of the corrected three-dimensional contrast enhanced images.

14. The ultrasound diagnosis apparatus according to claim 1, wherein the processor is further configured to change at least one of color tone and transparency of the contrast enhanced image in the first phase and the contrast enhanced image in the second phase when creating the composite image.

15. An ultrasound image processing apparatus comprising:
a processor connected to a memory,
wherein the processor is configured to:
calculate a movement distance between a tissue image in a first phase appearing after an ultrasound contrast agent is given to a subject and a tissue image in a second phase that is a phase later than the first phase;
create a corrected image from a contrast enhanced image in the first phase by matching the contrast enhanced image in the first phase in position with a contrast enhanced image in the second phase based on the movement distance;
create a composite image by combining the corrected image and the contrast enhanced image in the second phase; and
control a display unit to display the composite image, wherein
the tissue image in the first phase is an ultrasound image created by separating a fundamental wave corresponding to a transmission frequency of ultrasound waves transmitted from an ultrasound probe onto the subject in the first phase from reflected waves of the ultrasound waves in the first phase,
the tissue image in the second phase is an ultrasound image created by separating the fundamental wave corresponding to the transmission frequency of ultrasound waves transmitted from the ultrasound probe onto the subject in the second phase from reflected waves of the ultrasound waves in the second phase,
the contrast enhanced image in the first phase is an ultrasound image created by separating a subharmonic wave or a higher harmonic wave of the transmission frequency from the reflected waves used for creating the tissue image in the first phase, and
the contrast enhanced image in the second phase is an ultrasound image created by separating the subharmonic wave or the higher harmonic wave of the transmission frequency separated from the reflected waves used for creating the tissue image in the second phase.

16. An image processing method comprising:
calculating, using a processor, a movement distance between a tissue image in a first phase appearing after an ultrasound contrast agent is given to a subject, and a tissue image in a second phase that is a phase later than the first phase;
creating a corrected image from a contrast enhanced image in the first phase by matching the contrast enhanced image in the first phase in position with a contrast enhanced image in the second phase based on the movement distance;
creating a composite image by combining the corrected image and the contrast enhanced image in the second phase; and
controlling a display unit to display the composite image, wherein
the tissue image in the first phase is an ultrasound image created by separating a fundamental wave corresponding to a transmission frequency of ultrasound waves transmitted from an ultrasound probe onto the subject in the first phase from reflected waves of the ultrasound waves in the first phase,
the tissue image in the second phase is an ultrasound image created by separating the fundamental wave corresponding to the transmission frequency of ultrasound waves transmitted from the ultrasound probe onto the subject in the second phase from reflected waves of the ultrasound waves in the second phase, the contrast enhanced image in the first phase is an ultrasound image created by separating a subharmonic wave or a higher harmonic wave of the transmission frequency from the reflected waves used for creating the tissue image in the first phase, and the contrast enhanced image in the second phase is an ultrasound image created by separating the subharmonic wave or the higher harmonic wave of the transmission frequency separated from the reflected waves used for creating the tissue image in the second phase.

* * * * *